United States Patent [19]
Short

[11] Patent Number: 5,478,731
[45] Date of Patent: Dec. 26, 1995

[54] POLYCOS VECTORS

[75] Inventor: Jay M. Short, Encinitas, Calif.

[73] Assignee: Stratagene, La Jolla, Calif.

[21] Appl. No.: 133,179

[22] PCT Filed: Apr. 10, 1992

[86] PCT No.: PCT/US92/03012

§ 371 Date: Oct. 12, 1993

§ 102(e) Date: Oct. 12, 1993

[87] PCT Pub. No.: WO92/18632

PCT Pub. Date: Oct. 29, 1992

Related U.S. Application Data

[63] Continuation-in-part of Ser. No. 685,215, Apr. 12, 1991, abandoned.

[51] Int. Cl.[6] .............................. C12N 1/21; C12N 7/01; C12N 15/10; C12N 15/11

[52] U.S. Cl. ................ 435/91.4; 435/172.3; 435/252.33; 435/235.1; 435/252.3; 536/23.1

[58] Field of Search ...................... 435/91.32, 172.3, 435/320.1, 91.4, 252.33, 252.3, 235.1; 536/23.1

[56] References Cited

PUBLICATIONS

Ahmed (1989), Gene 75:315–321.
Evans et al. (1989), Gene 79:9–20.

*Primary Examiner*—Mindy B. Fleisher
*Assistant Examiner*—Philip W. Carter
*Attorney, Agent, or Firm*—Albert P. Halluin; Pennie & Edmonds

[57] ABSTRACT

A bacteriophage packaging site-based vector system is describe that involves cloning vectors and methods for their use in preparing multiple copy number bacteriophage libraries of cloned DNA. The vector is based on a DNA segment that comprises a nucleotide sequence defining a bacteriophage packaging site located between two termini having ligation means used to concatamerize fragments of DNA having compatible ligation means. Methods for preparing a concatameric DNA for packaging cloned DNA segments, and for packaging the concatamers to produce a library are also described.

18 Claims, 1 Drawing Sheet

FIG. 1

SEQUENCE LISTING ( 1 ) GENERAL INFORMATION:

( i i i ) NUMBER OF SEQUENCES: 13

( 2 ) INFORMATION FOR SEQ ID NO:1:

( i ) SEQUENCE CHARACTERISTICS:
        ( A ) LENGTH: 403 base pairs
        ( B ) TYPE: nucleic acid
        ( C ) STRANDEDNESS: unknown
        ( D ) TOPOLOGY: unknown     ( i i ) MOLECULE TYPE: DNA (genomic)

( x i ) SEQUENCE DESCRIPTION: SEQ ID NO:1:

```
GACATGAGGT  TGCCCCGTAT  TCAGTGTCGC  TGATTTGTAT  TGTCTGAAGT  TGTTTTTACG      60
TTAAGTTGAT  GCAGATCAAT  TAATACGATA  CCTGCGTCAT  AATTGATTAT  TTGACGTGGT     120
TTGATGGCCT  CCACGCACGT  TGTGATATGT  AGATGATAAT  CATTATCACT  TTACGGGTCC     180
TTTCCGGTGA  TCCGACAGGT  TACGGGGCGG  CGACCTCGCG  GGTTTTCGCT  ATTTATGAAA     240
ATTTTCCGGT  TTAAGGCGTT  TCCGTTCTTC  TTCGTCATAA  CTTAATGTTT  TTATTTAAAA     300
TACCCTCTGA  AAAGAAAGGA  AACGACAGGT  GCTGAAAGCG  AGGCTTTTTG  GCCTCTGTCG     360
```

TTTCCTTTCT CTGTTTTTGT CCGTGGAATG AACAATGGAA GTC    403

( 2 ) INFORMATION FOR SEQ ID NO:2:

( i ) SEQUENCE CHARACTERISTICS:
        ( A ) LENGTH: 461 base pairs
        ( B ) TYPE: nucleic acid
        ( C ) STRANDEDNESS: unknown
        ( D ) TOPOLOGY: unknown     ( i i ) MOLECULE TYPE: DNA (genomic)

( x i ) SEQUENCE DESCRIPTION: SEQ ID NO:2:

GTACGCGCCC TGTAGCGGCG CATTAAGCGC GGCGGGTGTG GTGGTTACGC GCAGCGTGAC    60

CGCTACACTT GCCAGCGCCC TAGCGCCCGC TCCTTTCGCT TTCTTCCCTT CCTTTCTCGC    120

CACGTTCGCC GGCTTTCCCC GTCAAGCTCT AAATCGGGGG CTCCCTTTAG GGTTCCGATT    180

TAGTGCTTTA CGGCACCTCG ACCCCAAAAA ACTTGATTAG GGTGATGGTT CACGTAGTGG    240

GCCATCGCCC TGATAGACGG TTTTTCGCCC TTTGACGTTG GAGTCCACGT TCTTTAATAG    300

TGGACTCTTG TTCCAAACTG GAACAACACT CAACCCTATC TCGGTCTATT CTTTTGATTT    360

ATAAGGGATT TTGCCGATTT CGGCCTATTG GTTAAAAAAT GAGCTGATTT AACAAAAATT    420

TAACGCGAAT TTTAACAAAA TATTAACGTT TACAATTTAA A    461

( 2 ) INFORMATION FOR SEQ ID NO:3:

( i ) SEQUENCE CHARACTERISTICS:
        ( A ) LENGTH: 66 base pairs
        ( B ) TYPE: nucleic acid
        ( C ) STRANDEDNESS: unknown
        ( D ) TOPOLOGY: unknown     ( i i ) MOLECULE TYPE: DNA (genomic)

( x i ) SEQUENCE DESCRIPTION: SEQ ID NO:3:

TATGGGGTTT TGCCAGACAA CTGGAACAGT TTCAGCGGAG TGCCAGTAGA ATGGAACAAC    60

TAAAGG    66

( 2 ) INFORMATION FOR SEQ ID NO:4:

( i ) SEQUENCE CHARACTERISTICS:
        ( A ) LENGTH: 12 base pairs
        ( B ) TYPE: nucleic acid
        ( C ) STRANDEDNESS: unknown
        ( D ) TOPOLOGY: unknown     ( i i ) MOLECULE TYPE: DNA (genomic)

( x i ) SEQUENCE DESCRIPTION: SEQ ID NO:4:

CCANNNNNT GG    12

( 2 ) INFORMATION FOR SEQ ID NO:5:

( i ) SEQUENCE CHARACTERISTICS:
        ( A ) LENGTH: 12 base pairs
        ( B ) TYPE: nucleic acid
        ( C ) STRANDEDNESS: unknown
        ( D ) TOPOLOGY: unknown     ( i i ) MOLECULE TYPE: DNA (genomic)

( x i ) SEQUENCE DESCRIPTION: SEQ ID NO:5:

GGTNNNNNNA CC    12

( 2 ) INFORMATION FOR SEQ ID NO:6:

( i ) SEQUENCE CHARACTERISTICS:
  ( A ) LENGTH: 6 base pairs
  ( B ) TYPE: nucleic acid
  ( C ) STRANDEDNESS: unknown
  ( D ) TOPOLOGY: unknown  ( i i ) MOLECULE TYPE: DNA (genomic)

( x i ) SEQUENCE DESCRIPTION: SEQ ID NO:6:

CYCGRG     6

( 2 ) INFORMATION FOR SEQ ID NO:7:

( i ) SEQUENCE CHARACTERISTICS:
  ( A ) LENGTH: 6 base pairs
  ( B ) TYPE: nucleic acid
  ( C ) STRANDEDNESS: unknown
  ( D ) TOPOLOGY: unknown  ( i i ) MOLECULE TYPE: DNA (genomic)

( x i ) SEQUENCE DESCRIPTION: SEQ ID NO:7:

GGYRCC     6

( 2 ) INFORMATION FOR SEQ ID NO:8:

( i ) SEQUENCE CHARACTERISTICS:
  ( A ) LENGTH: 6 base pairs
  ( B ) TYPE: nucleic acid
  ( C ) STRANDEDNESS: unknown
  ( D ) TOPOLOGY: unknown  ( i i ) MOLECULE TYPE: DNA (genomic)

( x i ) SEQUENCE DESCRIPTION: SEQ ID NO:8:

GRGCYC     6

( 2 ) INFORMATION FOR SEQ ID NO:9:

( i ) SEQUENCE CHARACTERISTICS:
  ( A ) LENGTH: 8 base pairs
  ( B ) TYPE: nucleic acid
  ( C ) STRANDEDNESS: unknown
  ( D ) TOPOLOGY: unknown  ( i i ) MOLECULE TYPE: DNA (genomic)

( x i ) SEQUENCE DESCRIPTION: SEQ ID NO:9:

GAAATGCN     8

( 2 ) INFORMATION FOR SEQ ID NO:10:

( i ) SEQUENCE CHARACTERISTICS:
  ( A ) LENGTH: 11 base pairs
  ( B ) TYPE: nucleic acid
  ( C ) STRANDEDNESS: unknown
  ( D ) TOPOLOGY: unknown  ( i i ) MOLECULE TYPE: DNA (genomic)

( x i ) SEQUENCE DESCRIPTION: SEQ ID NO:10:

GCCNNNNNGG C     11

( 2 ) INFORMATION FOR SEQ ID NO:11:

( i ) SEQUENCE CHARACTERISTICS:
  ( A ) LENGTH: 12 base pairs ( B ) TYPE: nucleic acid
           ( C ) STRANDEDNESS: unknown
           ( D ) TOPOLOGY: unknown ( i i ) MOLECULE TYPE: DNA (genomic)

( x i ) SEQUENCE DESCRIPTION: SEQ ID NO:11:

CCANNNNNT GG 12

( 2 ) INFORMATION FOR SEQ ID NO:12:

( i ) SEQUENCE CHARACTERISTICS:
           ( A ) LENGTH: 9 base pairs
           ( B ) TYPE: nucleic acid
           ( C ) STRANDEDNESS: unknown
           ( D ) TOPOLOGY: unknown ( i i ) MOLECULE TYPE: DNA (genomic)

( x i ) SEQUENCE DESCRIPTION: SEQ ID NO:12:

CACNNNGTG 9

( 2 ) INFORMATION FOR SEQ ID NO:13:

( i ) SEQUENCE CHARACTERISTICS:
           ( A ) LENGTH: 13 base pairs
           ( B ) TYPE: nucleic acid
           ( C ) STRANDEDNESS: unknown
           ( D ) TOPOLOGY: unknown ( i i ) MOLECULE TYPE: DNA (genomic)

( x i ) SEQUENCE DESCRIPTION: SEQ ID NO:13:

GGCCNNNNNG GCC 13

POLYCOS VECTORS

CROSS REFERENCE TO RELATED APPLICATIONS

This application is the national phase application of international application PCT/US92/03012, which was filed under the PCT on Oct. 29, 1992, and which is a continuation-in-part of U.S. application Ser. No. 07/685,215, filed Apr. 12, 1991, now abandoned.

TECHNICAL FIELD

The present invention relates to recombinant DNA cloning vectors that utilize a bacteriophage packaging site to increase cloning and transfer of nucleic acids using bacteriophage-based vectors.

BACKGROUND

Cosmid and lambda phage-based cloning vectors include a nucleotide sequence termed the "cos site" which provides a signal for packaging the nucleic acid into a lambda phage particle. Both cosmids and lambda vectors utilize the cos site and therefore share the cloning efficiency afforded lambda phage-based cloning systems.

Cloning DNA segments by using lambda bacteriophage (phage) vectors provides an important tool in molecular biology, particularly due to the efficiency of the cloning procedure and the size of the library of DNA segments that can be constructed and propagated when using lambda vectors. The high efficiency of cloning with lambda phage vectors has been unsurpassed by other vectors for almost a decade. This is primarily due to the existence of efficient in vitro lambda packaging extracts that can achieve up to ten percent of the theoretical limit of $2\times10^{10}$ plaque forming units (pfu) per microgram (ug) of lambda DNA. Lambda phage, or lambda, have been developed as vectors to clone large populations (libraries) of DNA segments, typically 2 to 35 kb in length.

Cosmids were developed as a shuttle type vector designed to move large cloned DNA segments, typically 15 to 50 kilobases (kb) in length, from an initial cosmid phage library to a bacterial plasmid cloning system. Cosmids typically contain a plasmid origin of replication to allow propagation in a bacterial cell as a plasmid. However, cosmids are difficult to work with in bacteria because their large size is not readily propagated in a bacterial host, and they are susceptible to recombination and loss of original sequence integrity in the cloned DNA segment.

Both cosmid and lambda vectors typically carry a single cloned DNA segment per bacteriophage particle, and therefore the cloned DNA segment can readily be isolated away from other members of the library by isolating single phage particles and propagating them as single colonies. Other cloning vectors that utilize a cos site have been described. See for example, Ahmed et al, *Gene,* 75:315–321(1989); Wahl et al, *Proc. Natl. Acad. Sci. USA,* 84:2160–2164 (1987); and Evans et al, *Gene,* 79:9–20(1989).

The library size obtainable using the efficient cos-based phage system is limited by the efficiency of packaging, and by the amount of phage particles that can be conveniently manipulated. No system has yet been described where multiple recombinant DNA molecules, each representing a distinct member of the library being prepared, are present in a single phage particle. Such a system would increase the library size by a multiple of the number of DNA molecule species packaged per phage particle.

BRIEF SUMMARY OF THE INVENTION

It has now been discovered that the cos packaging signal from phage lambda can be utilized in a polycos vector system that increases the number of DNA segments that can be cloned into a single phage particle, thereby increasing the effective library size. The system is generally applicable to a system of vectors based on bacteriophage packaging sites.

The present invention provides a system to prepare a population of DNA molecules suitable for packaging into phage lambda using conventional in vitro packaging extracts to form lambda phage particles, or lambda particles. The prepared DNA molecule comprises multiple cos sites each alternating with inserted DNA segments in a linear form. The prepared DNA molecule is produced using a "polycos vector" of the present invention which is a linear molecule having a single intact lambda cos site and ligatable termini that can produce a concatameric ligation product. Through ligation of the linear vector with a population of DNA segments to be cloned (i.e., "insert DNA") at high concentrations, concatamers (polymers) of the linear vector are generated having alternating cos and insert nucleotide sequences. The concatamerized molecule satisfies the requirement for a substrate suitable for lambda packaging.

Lambda packing extract operates by selecting a "first" cos site at random and then scanning down the DNA molecule until it encounters a "second" cos site in the proper orientation that is greater than 38 kilobases (kb) from the first cos site. This "second" cos site will only be detected after the lambda phage head is approximately full, i.e., greater than 38 kb. Due to this size requirement for packaging, multiple cos sites and alternating inserted DNA segments are packaged into a single phage head that occur between the "first" cos-site and the "second" cos site on the DNA molecule. A typical concatamer of from about 38 to 51 kb in length can be packaged into a single lambda head, depending on the strain. Using the polycos vector where the linear vector containing the cos site is approximately 5 kb and the insert DNA is approximately 2 kb as an example, a total of 6 to 7 insert DNA segments can be packaged into a single lambda head in the present polycos vector system.

Thus, in one embodiment the invention contemplates a DNA molecule of about no more than 26,000 nucleotides in length comprising a sequence of nucleotides that defines a cos site located between two restriction endonuclease sites such that, upon cleavage, forms a DNA segment having ligatable termini. Preferably, the termini are non-complementary, and more preferably the two restriction sites are non-palindromic restriction endonuclease sites.

Because the present invention increases the cloned DNA segment library size without increasing the number of phage particles in the library, the present polycos vector system is applicable to a variety of recombinant DNA methodologies. These methods include cloning a single copy gene or DNA segment from genomic DNA, cloning a specific messenger RNA (mRNA) molecule by first preparing a cDNA library, producing a library of random oligonucleotides to form synthetic peptides, or a library of aptamers (protein-binding oligonucleotides), and producing libraries of immunoglobulin variable region heavy chain or light chain gene coding DNA segments. The polycos vector system also is applicable to protein modeling and engineering strategies when those strategies involve drawing on libraries of protein epitopes or peptides.

An additional benefit to polycos vector-based cloning systems is that DNA segment libraries can be propagated without the need to introduce the library into a host cell using DNA transformation or electroporation methods, which are less efficient than infection using phage particles on susceptible host cells.

BRIEF DESCRIPTION OF THE DRAWINGS

In the drawings, forming a portion of this disclosure:

FIG. 1 is a flow diagram illustrating the methods of producing a polycos concatamer and the packaging of the concatamer to produce a phage library of this invention, with the arrows depicting steps in the method. In the embodiment depicted, the polycos vector (PC1) contains a filamentous phage (Ff) origin of replication (Ff ori) derived from M13 (shaded circle). The cos site is shown as a small black rectangle. In the first step, PC1 is linearized using BstXI and is shown to contain a Ff Ori site and a cos site (black bar). Second, the linearized PC1 polycos vector is ligated with an insert DNA segment. The insert is depicted as a black segment having a white bar to indicate the orientation of the insert sequences. Both the vector and the insert have non-palindromic cohesive termini, and the resulting polycos multimer (concatamer) contains alternating vector and insert segments that are all in one orientation. The dotted line indicates the sequence defining a single M13 phage or fl cosmid genome that could be produced by Ff helper rescue, and includes one insert DNA segment. The solid line indicates the multimeric sequence selected by a lambda phage head between 38 and 51 kb in length and between two cos sites. Packaging of a multimeric portion of the polycos multimer to form a library of this invention is depicted in the third step. The fourth step depicts the process of infecting an *E. coli* host with the lambda phage library, and the fifth step depicts the process of producing a library of Ff, each containing one of the DNA inserts introduced into the concatamer.

DETAILED DESCRIPTION OF THE INVENTION

A. Definitions

Base Pair: a partnership of adenine (A) with thymine (T), or of cytosine (C) with guanine (G) in a double-stranded DNA molecule. In RNA, uracil (U) is substituted for thymine. Base pairs are said to be "complementary" when their component bases pair up normally when a DNA or RNA molecule adopts a double-stranded configuration.

Complementary Nucleotide Sequence: a sequence of nucleotides in a single-stranded molecule of DNA or RNA that is sufficiently complementary to another single strand to specifically (non-randomly) hybridize to it with consequent hydrogen bonding.

Conserved: a nucleotide sequence is conserved with respect to a preselected (reference) sequence if it non-randomly hybridizes to an exact complement of the preselected sequence.

Duplex DNA: a double-stranded nucleic acid molecule comprising two strands of substantially complementary polynucleotides held together by one or more hydrogen bonds between each of the complementary bases present in a base pair of the duplex. Because the nucleotides that form a base pair can be either a ribonucleotide base or a deoxyribonucleotide base, the phrase "duplex DNA" refers to either a DNA-DNA duplex comprising two DNA strands (dsDNA), or an RNA-DNA duplex comprising one DNA and one RNA strand.

Fusion Protein: A protein comprised of at least two polypeptides. In some cases, a linking sequence is present to operatively link the two polypeptides into one continuous polypeptide (i.e., fusion protein). At least one, and preferably two, of the polypeptides comprising a fusion protein is biologically active. The two polypeptides linked in a fusion protein are typically derived from two independent sources, and therefore a fusion protein comprises two linked polypeptides not normally found linked in nature.

Gene: a nucleic acid whose nucleotide sequence codes for a RNA, DNA or polypeptide molecule. Genes may be uninterrupted sequences of nucleotides or they may include such intervening segments as introns, promoter regions, splicing sites and repetitive sequences. A gene can be either RNA or DNA.

Hybridization: the pairing of complementary nucleotide sequences (strands of nucleic acid) to form a duplex, heteroduplex, or complex containing more than two single-stranded nucleic acids, by establishing hydrogen bonds between/among complementary base pairs. Hybridization is a specific, i.e., non-random, interaction between/among complementary polynucleotides that can be competitively inhibited.

Linking Sequence: an amino acid residue sequence comprising at least one amino acid residues. A linking sequence serves to chemically link two disparate polypeptides via a peptide bond between the linking sequence and each of the polypeptides.

Nucleotide: a monomeric unit of DNA or RNA consisting of a sugar moiety (pentose), a phosphate group, and a nitrogenous heterocyclic base. The base is linked to the sugar moiety via the glycosidic carbon (1' carbon of the pentose) and that combination of base and sugar is a nucleoside. When the nucleoside contains a phosphate group bonded to the 3' or 5' position of the pentose, it is referred to as a nucleotide. A sequence of operatively linked nucleotides is typically referred to herein as a "base sequence" or "nucleotide sequence", and their grammatical equivalents, and is represented herein by a formula whose left to right orientation is in the conventional direction of 5'-terminus to 3'-terminus.

Nucleotide Analog: a purine or pyrimidine nucleotide that differs structurally from an A, T, G, C, or U base, but is sufficiently similar to substitute for the normal nucleotide in a nucleic acid molecule. Inosine (I) is a nucleotide analog that can hydrogen bond with any of the other nucleotides, A, T, G, C, or U. In addition, methylated bases are known that can participate in nucleic acid hybridization.

Polynucleotide: a polymer of single or double stranded nucleotides. As used herein "polynucleotide" and its grammatical equivalents will include the full range of nucleic acids. A polynucleotide will typically refer to a nucleic acid molecule comprised of a linear strand of two or more deoxyribonucleotides and/or ribonucleotides. The exact size will depend on many factors, which in turn depends on the ultimate conditions of use, as is well known in the art. The polynucleotides of the present invention include primers, probes, RNA/DNA segments, oligonucleotides or "oligos" (relatively short polynucleotides), genes, vectors, plasmids, and the like.

Polypeptide or Peptide or Protein: a linear series of at least two amino acid residues in which adjacent residues are connected by peptide bonds between the alpha-amino group of one residue and the alpha- carboxy group of an adjacent residue.

Recombinant DNA (rDNA) molecule: a DNA molecule produced by operatively linking a nucleic acid sequence, such as a gene, to a DNA molecule sequence of the present invention. Thus, a recombinant DNA molecule is a hybrid DNA molecule comprising at least two nucleotide sequences not normally found together in nature. rDNA's not having a common biological origin, i.e., evolutionarily different, are said to be "heterologous".

Vector: a DNA molecule capable of autonomous replication in a cell and to which a DNA segment, e.g., gene or polynucleotide, can be operatively linked so as to bring about replication of the attached segment. Vectors capable of directing the expression of genes encoding for one or more proteins are referred to herein as "expression vectors". Particularly important vectors allow cloning of cDNA (complementary DNA) from mRNAs produced using reverse transcriptase.

B. DNA Molecules

The present invention describes a DNA molecule that is useful in a polycos vector cloning system of this invention. The DNA molecule comprises a sequence of nucleotides that defines a lambda phage cos site at a position on the DNA molecule between two restriction endonuclease sites. The two restriction endonuclease sites, designated a first and second restriction site, upon cleavage by their corresponding restriction endonucleases, form a DNA segment containing the cos site between first and second cohesive termini.

Preferably, the overhang in the first terminus is not complementary to the overhang at the second terminus to prevent self-ligation of the DNA segment. More preferably, there are at least two, and more preferably at least three nucleotide bases in the overhang of the first terminus that are not complementary to the overhang of the second terminus.

In preferred embodiments, the two restriction endonuclease sites on a DNA molecule of this invention flanking a cos site are non-palindromic restriction endonuclease sites, also referred to herein as NPRE sites. A non-palindromic restriction endonuclease (NPRE) site is defined herein as a sequence of nucleotides in a double stranded DNA molecule that is recognized and cleaved by a specific restriction endonuclease to form two cohesive (overhanging and complementary) termini which do not spell out the same nucleotide sequence when read in the direction of 5' to 3'.

Restriction endonucleases specific for an NPRE site are well known in the art and include at least the restriction enzymes Aoc I, AvaI, BanI, BanII, BsmI, BglI, BstEII, BstXI, DdeI, DraII, DraIII, EspI, HinfI, MstII, ScrFI, Sau96I, SfiI and TthIIII. Other restriction enzymes may be developed that recognize a NPRE site and are therefore also contemplated.

In preferred embodiments a DNA molecule of this invention contains a NPRE site in which the number of nucleotides in the overhanging portion of the cohesive termini is at least two, preferably three, and more preferably is four or more. A larger overhang provides a larger number of nucleotides to base pair in the ligation reaction, thereby increasing the affinity of the cohesive termini for their complement.

Also preferred are NPRE sites where less than 50 percent, and preferably none, of the nucleotides in an overhanging sequence are the same nucleotide base residue(s) as the residue on the complementary strand at that same position. The fewer positions in the overhang which are occupied by the same nucleotide in both strands at the corresponding position, the less likely a hybridization will occur with an unintended cohesive termini. This condition favors ligation between complementary termini.

For example, the BstXI site in a dsDNA can be represented as:

5'-CCANNNNNNTGG-3' (SEQ ID NO:4)
3'-GGTNNNNNNACC-5' (SEQ ID NO:5)

where the overhang created by cleavage can be represented as

5'-CCANZZZZ     NTGG-3'
3'-GGTN     ZZZZNACC-5', where "Z" represents an "N" in the overhang region. If "ZZZZ" is selected to be "GATC" or "AATT" the site is palindromic If "ZZZZ" is selected to be "GACT" for example, the site is completely non palindromic. If "ZZZZ" is selected to be "GAGC" the site is 50% non-palindromic, because the first and last residues (ie, the first G and the C) are complementary and-so only half of the four overhanging residues are effectively palindromic.

Preferred NPRE sites are those recognized by the enzymes SfiI, DraIII, BstXI, BglI, BsmI, BanII, BanI, and AvaI, and particularly the enzymes SfiI, DraIII, BstXI and BglI, where the NPRE site nucleotides present in the "N" positions are selected as to present three or more non-palindromic residues in the overhang. The recognition specificities of preferred candidate restriction enzymes for an NPRE site of the invention are shown in Table I.

TABLE 1

| Potential Non-Palindromic Recognition Sites | |
|---|---|
| Restriction Endonuclease | Recognition Sequence[a] |
| Ava I | CPyCGPuG (SEQ ID NO:6) |
| Ban I | GPyCGPuC (SEQ ID NO:7) |
| Ban II | GPuGCPyC (SEQ ID NO:8) |
| BsmI | GAAATGCN (SEQ ID NO:9) |
| BglI | GCCNNNNNGGC (SEQ ID NO: 10) |
| BstXI | CCANNNNNNTGG (SEQ ID NO:11) |
| DraIII | CACNNNGTG (SEQ ID NO:12) |
| SfiI | GGCCNNNNNGGCC (SEQ ID NO:13) |

[a]Py = C or T, Pu = A or G, N = A, G, C or T, and the underline indicates the overhang region of the cohesive termini after cleavage of a dsDNA molecule having the recognition sequence.

In one embodiment, a DNA molecule contains two NPRE sites that can be cleaved by the same restriction endonuclease, thereby simplifying the digestion by requiring one, rather than two, restriction enzymes. This feature is possible where the first and second NPRE sites are selected to have different nucleotide sequences in the overhang region and thereby do not produce cohesive termini that can hybridize between the first and second NPRE sites. Exemplary are the BstXI first and second NPRE sites described in Example 3.

A DNA molecule of this invention can be a circular or linear molecule. In the case of a circular molecule, the two NPRE sites are separated by an intervening sequence of nucleotides that are typically non-essential to the function of the polycos vector. The intervening sequence becomes disattached upon cleavage of the DNA molecule at the two NPRE sites, and a DNA segment of this invention is formed having a cos site positioned between the two NPRE sites at its termini in the form of first and second cohesive ends. The intervening sequence, also referred to as a stuffer sequence or stuffer fragment after cleavage, preferably has a very short length nucleotide to facilitate its separation after cleavage from the cos-containing linear DNA segment. Typical lengths range from only the few residues necessary to form two NPRE sites up to several hundred nucleotide bases, and preferably is about 10 to 50 nucleotides in length. Exemplary is the stuffer sequence between the two BstXI sites defined by the polycos vector system described in Example 3.

In another embodiment, the stuffer fragment can contain a genetic element to confer additional properties to the polycos vector system. Exemplary are selectable markers, shuttle vector functions such as origins of replication for other systems such as bacterial plasmids or filamentous phage, and negative selection markers such as a toxic gene, amber codons, or the lambda kill gene, and the like genetic elements.

A linear DNA molecule of this invention comprises a linear sequence of nucleotides that defines a cos site at a position on the molecule between two NPRE sites as described for a circular DNA molecule of this invention.

Also contemplated is a DNA segment that comprises a sequence of nucleotides that defines a cos site at a position on the DNA segment between two non-palindromic and non-complementary first and second cohesive termini.

A DNA molecule or DNA segment of this invention can be a variety of lengths to accommodate additional genetic elements, as is well known, according to the design of the polycos vector to provide desired features as described further herein. Insofar as the lambda phage particle can accommodate approximately 36 to 56 kilobases (kb) of nucleic acid in a packaging reaction, two cos-flanked units can be packaged in one phage particle each having a length of up to 26 kb. However, because as an important feature is to facilitate a maximum library size by providing the maximum number of DNA inserts to be packaged per lambda particle, smaller DNA molecules or DNA segment lengths are preferred. Typically a DNA molecule or DNA segment of this invention is less than 10,000 nucleotides in length, preferably less than 5,000 nucleotides, and in some embodiments can be less than 2,000 nucleotides in length. Shorter lengths are particularly preferred where the purpose is to facilitate the maximum number of polycos units to be packaged per lambda particle.

A phage lambda cos site, or cos site, is well characterized in the art, and is a sequence of nucleotides that provides a recognition site during lambda phage particle head "packing" that determines the DNA molecule to be packaged into the particle, and its approximate size. The manner in which cos functions has been extensively studied, and involves binding of the DNA molecule to the lambda DNA cleavage enzyme terminase, binding the phage "prohead" particle and cleavage of the DNA. See, for example Feiss et al., in "Lambda II" Hendrix et al., eds., Cold Spring Harbor Laboratory Press, Cold Spring Harbor, N.Y. p. 309 (1983). Although any sequence that controls lambda phage packaging in a manner defined by the natural lambda cos site could be utilized in the present invention, the cos site sequence derived from field isolates of lambda and their functional equivalents are preferred. Preferred sequences defining a cos site are defined by the 400 base pair(bp) HincII fragment described by Meyerowitz et al., *Gene*, 11:271 (1980). The Hinc II fragment containing the cos site spans nucleotide base 48298 to nucleotide base 199 of the lambda genome. Particularly preferred is a sequence that corresponds to, and preferably is identical to the sequence shown in SEQ ID NO. 1 from nucleotide base 1 to base 403.

In one embodiment, the present invention is not limited to the use of the cos site as the bacteriophage particle packaging signal. Other bacteriophage systems have been described that define the packaging of phage DNA into the phage particle by a packaging site. For example, the pac sequence for bacteriophage P1 has been characterized and functions as a site that initiates packaging of DNA into the bacteriophage P1 particle. Sternberg et al., *Proc. Natl. Acad, Sci. USA*, 87:8070–8074 (1990). The minimum nucleotide sequence required to function as a pac site is 162 nucleotides in length. The 162 nucleotide sequence defining the bacteriophage P1 pac site can be used in place of the cos site to produce a cloning vector according to the methods of the present invention. This "polypac" vector is packaged into P1 bacteriophage particles using a P1 packaging extract as described by Sternberg et al., *Proc. Natl. Acad. Sci, USA*, 87:103–107 (1990). Bacteriophage P1 particles can accommodate up to 102 kb of genomic DNA before the particle head is full. Thus polypac cloning systems based on bacteriophage P1 can be produced according to the present methods that have an even greater cloning capacity than those based on bacteriophage lambda.

In a related embodiment, the invention contemplates a cloning system that utilizes a bacteriophage packaging site in place of cos or pac in combination with a packaging extract compatible with the packaging site. The packaging site contemplated is one associated with any of a variety of bacteriophage that functions on a particle head filling mechanism that packages until the head is full after sensing the initiator packaging site. Exemplary bacteriophages having a contemplated packaging site include the temperate bacteriophages P22, P1, P2, P4, T4, T5, T7, lambda and the like.

Thus the invention is not to be construed to be limited to polymeric packaging of nucleic acid units based on a cos site concatamer as described herein. Lambda phage particles each have a packaging capacity of about 36 to 56 kb, thereby accommodating two cos-site flanked nucleic acid units of about 26 kb or less.

Similar calculations of capacity , i.e., the "genome length", can be made for the many other known bacteriophage available for practicing the present invention. For instance, the range of total nucleic acid that can be packaged in a bacteriophage particle is from about 25 percent below to about 10 percent above the average genome size of the wild type bacteriophage. Wild type genome sizes for known bacteriophages include P4 (10.5 kb), P22 (42 kb), P1 (88 kb), P2 (33 kb), T4 (166 kb), T5 (113 kb), and T7 (40 kb).

Thus a DNA segment of the present invention can comprise a sequence of nucleotides that defines a bacteriophage packaging site located between first and second termini each having ligation means. Preferably, the DNA segment has a minimum length to allow for the concatamerization of a maximum number of inserts into a single "genome length" for packaging. Typically, the length is at least 500 nucleotide bases, and preferably longer to combine the various vector components described herein.

Ligation means can be blunt ends, to accommodate blunt end ligation, cohesive termini, to drive ligation, or more preferably complementary termini selected to direct ligation in an alternating first and second DNA segment order as described herein.

In preferred embodiments, the polycos vector system is designed not only to provide for packaging of multiple DNA inserts into a single lambda phage particle, but to allow for convenient manipulation of the cloned inserts. Additional elements are therefore contemplated as components of a DNA molecule or DNA segment of this invention which provide particular preferred features and therefore represent preferred embodiments.

Figure 1:
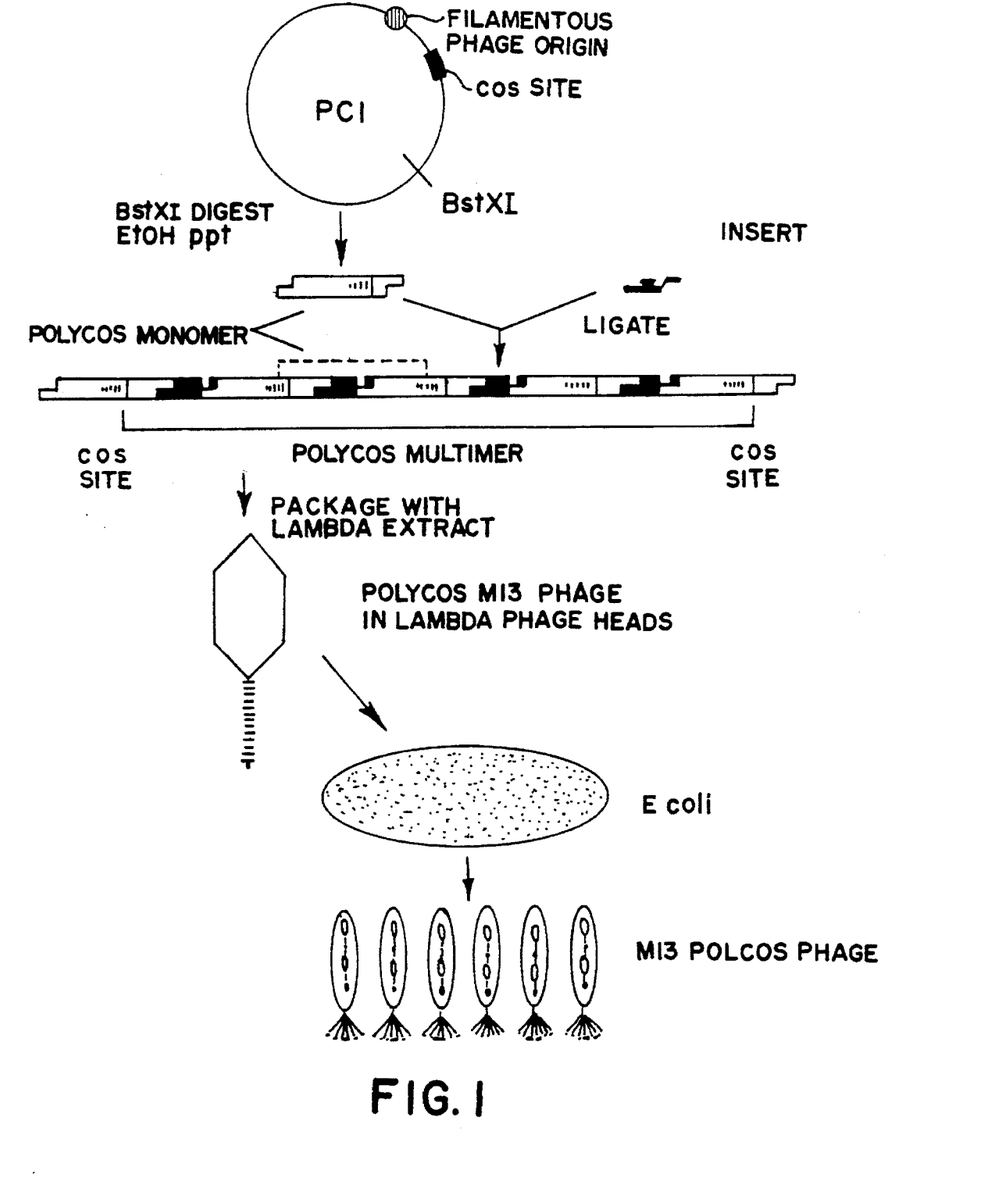

For example, the presence of a filamentous phage (Ff) origin of replication allows the rescue of a sequence of nucleotides located within the packaged DNA molecule concatamer. Thus, in one embodiment, a DNA molecule or segment of this invention contains a filamentous phage origin of replication, such as the origin of replication (Ori) from M13, f1, fd and the like. In this embodiment, a filamentous phage Ori, also referred to as Ff Ori, provides in a polycos concatamer DNA molecule multiple Ff Ori sites, one at each cos-containing segment. Thus, in the presence of genetic complementation, such as by rescue with a helper filamentous phage, the concatamer will provide a template for replication of each DNA insert separately from each adjacent Ff Ori, thereby producing separate circular DNA molecules having the nucleotide sequence corresponding to the sequence between two adjacent Ff Ori on the concatamer. A representative sequence is depicted by the dotted line over the concatamer shown in FIG. 1. By a subsequent "rescue" manipulation of the *E. coli* library infected with lambda particles, having concatameric polycos DNA molecules packaged and containing multiple DNA inserts, one can conveniently isolate separate circular DNA molecules, each containing a single DNA insert and Ff Ori.

The plus strand origin of replication for phage f1 has been well characterized and can be utilized as exemplary of a Ff Ori for use in the present invention. Ff Ori comprises a sequence of nucleotides that define a site for initiation of DNA replication (i.e., initiators). Exemplary initiators are sequences of about 130 to 140 nucleotides in length as described by Horiuchi, *J. Mol. Biol.*, 188:215–223 (1986), and Brenner et al., *Gene*, 17:27–44 (1982). A preferred initiator sequence of an Ff Ori is shown in SEQ. ID NO 2 from base 240 to base 461 that corresponds to bases 5776 to 5947 of the f1 Ff Ori shown in FIG. 3 of Short et al., *Nucleic Acids. Res.*, 16:7583–7600 (1988).

Other origins of replication may also be used to accomplish rescue, as is well known, and include ike, phi-x and the like bacteriophage origins of replication.

Thus, one embodiment contemplates a DNA molecule or segment of this invention that further contains a sequence of nucleotides that defines a filamentous phage origin of replication. Exemplary is the phagescript-cos construct described in Example 2.

A feature complementary to the ability to isolate single insert-containing circular DNA molecules is the ability to package those circular DNA molecules into separate phage particles for subsequent propagation. Thus one embodiment contemplates a DNA molecule or DNA segment of this invention that further contains between the two NPRE sites both a filamentous phage origin of replication together with a sequence of nucleotides that defines a filamentous phage packaging site. Constructs having both a Ff Ori and the packaging site for filamentous phage provide the capacity to rescue infectious filamentous phage from the *E. coli* library first produced with lambda as described above. The rescued filamentous phage each contain a single DNA insert formed by the action of Ff Ori as described before.

This embodiment of a DNA molecule or DNA segment of this invention that further contains both a Ff Ori and a packaging site for filamentous phage is particularly preferred because it facilitates (1) construction of bigger libraries due to the polycos vector in lambda, (2) simplified screening by DNA hybridization of multiple inserts per lambda phage plaques in plaque hybridization protocols, and (3) the ability to rescue the single DNA insert by filamentous phage rescue and subsequent screening by filamentous phage plaque hybridization. This embodiment is suited for cDNA cloning of mRNA from complex populations of mRNA, for cloning DNA fragments from genomic DNA and related cloning manipulations involving screening large libraries for relatively rare genes or other genetic elements. Preparation of a filamentous phage containing a single insert is also useful for sequencing the cloned insert, for mutagenesis of the cloned gene and for gene expression, as is well known.

A filamentous phage packaging site is well characterized in the art and is a discreet genetic element separate from a Ff Ori, although the two elements are typically located very close to each other on wild type strains of filamentous phage. For a description of filamentous phage packaging sites and Ff Ori sites, see Rasched et al., *Microbiol. Rev.*, 50:401–427 (1986); Horinuhi, *J. Mol. Biol.*, 188:215–223 (1986); and Short et al., *Nucl. Acids Res.*, 16:7583–7600 (1988).

Other filamentous phage packaging sites can be utilized in place of the above described packaging site such as the packaging site derived from phi-x or Ike. The Ike phage packaging signal can be used by any of the F-pili specific phages. Peters et al., *DNA*, 6:139–147 (1987).

Preferred sequences of nucleotides for use in the present invention that contain a filamentous phage packaging site are described in Short et al., *Nucl. Acids Res.*, 16:7583–7600 (1988) shown in SEQ ID No. 2 from base 1 to base 110. A particularly preferred DNA molecule contains overlapping Ff Ori and packaging sites as shown by SEQ. ID NO. 2 from base 1 to base 461.

The relative location of the cos site, the Ff Ori site or the filamentous phage packaging site to each other on a DNA molecule of this invention is not critical so long as all the named genetic elements are located between the two NPRE sites. Typically these elements are defined on the DNA molecule segment of this invention with only a sufficient number of nucleotides intervening between the elements to present convenient restriction endonuclease sites for the assembly of the elements into a single sequence of nucleotides. Where Ff Ori and the filamentous phage packaging site are derived from a single strain, it is convenient, and therefore preferred, that they be defined by a sequence of nucleotides corresponding to the sequence of nucleotides of a field strain of filamentous phage that defines these two elements.

Helper filamentous phage suitable for use to rescue Ff Ori-containing genomes can be a variety of strains, including wild type M13, f1 or fd and mutant strains such as M13mp19, VCS-M13 (Stratagene) and the like.

As an alternative to using Ff Ori and a Ff packaging site, there are other systems available to rescue a single gene insert out from a library of genes produced by polycos. For example, using a flp recombinase system comprising the flp recognition sites (FRS) and the flp recombinase, one can initiate excision of a single gene located between FRS sites. For a description of the flp system, see Belfort et al., *Cold Spring Harbor Symposium on Quantitative Biology*, 52:181 (1987); Amin et al., *Mol. Cell. Biol.*, 9:1987–1995 (1989); and Meyer-Leon et al., *Mol. Cell. Biol.*, 10:235–242 (1990). A different selective recombination system suitable for use in place of Ff Ori and Ff packaging signals is the cre-lox site-specific recombination system of coliphage P1. For a complete description of cre-lox see Sauer, *Mol. Cell. Biol.*, 7:2087–2095 (1987); Sauer et al., *The New Biol.*, 2:441–449 (1990); Hoess et al., *J. Mol. Biol.*, 181:351–362 (1985); and Huess et al., *Gene*, 40:325–329 (1985). A vector designated Ad10 containing the elements of the cre-lox system is also available commercially from Dupont (Boston, Mass.).

Other elements for inclusion in a DNA molecule or segment of this invention can include a procaryotic origin of replication site, such as the bacterial ColE1 Ori, a selectable marker gene such as drug resistance genes for resistance to ampicillin (Amp<sup>r</sup>) tetracycline (Tet<sup>r</sup>), chloramphenicol (Cam<sup>r</sup>) and the like, and gene expression elements for producing expressed fusion genes. The benefits of including these various genetic elements to a DNA molecule or DNA segment of this invention are well understood and are widely used in the recombinant DNA vector arts. See for example *Molecular Cloning: A Laboratory Manual, Second Edition,* Sambrook et al., eds., Cold Spring Harbor Laboratory Press, Cold Spring Harbor, N.Y. (1989); and Vectors: *A Survey of Molecular Cloning Vectors and Their Uses,* Rodriguez et al., eds., Butterworth Publishers, Boston, Mass. (1988).

Other plasmid origins of replication (replicons) can be used in place of ColE1, so long as they provide the basic function of specifying that DNA replication initiate and subsequently terminate after a defined process of DNA replication. Preferred replicons besides ColE1 include IncFII-type replicons described by Womble et al., *J. Mol. Biol.,* 181:395 (1985), pT181 replicons described by Kumar et al., *Proc. Natl. Acad. Sci, USA,* 82:638 (1985), RK2 replicons described by Thomas et al in "Plasmids in Bacteria" Helinski et al., eds. p 261, Plenum Press (New York, N.Y., 1985), RK6 replicons described by Filutowicz et al., in "Plasmids in Bacteria", supra, and the like. See "Plasmids, a Practical Approach" Hardy ed., IRL Press (Washington, D.C.) (1987) for a review of bacterial replicons.

The use of genetic elements in the present polycos vectors for expressing fusion genes is particularly preferred because of the recent developments in methods for designing synthetic protein epitopes. The ability to screen larger libraries of synthetic epitopes is one benefit to the technology when polycos vectors are used. For descriptions of fusion protein technologies, see "Gene Expression Technology" in *Meth. Enzymol.,* Volume 185 (1990). For descriptions of the use of filamentous phage gene III or gene VIII protein to form fusion proteins for synthetic epitope mapping methods, see Parmely et al, *Gene* 73:305–318 (1988); Scott et al, *Science,* 249:386–390 (1990); Devlin et al., *Science,* 249:404–406 (1990); and Cwirla et al., *Proc. Natl. Acad. Sci. USA,* 87:6378–6382 (1990).

As used herein, the term "vector" refers to a nucleic acid molecule capable of transporting between different genetic environments another nucleic acid to which it has been operatively linked. Preferred vectors are those capable of autonomous replication of themselves and the DNA inserts to which they are operatively linked. As used herein, the term "operatively linked", in reference to DNA inserts, describes that the nucleotide sequence of the insert is joined to the vector so that the sequence of the insert is under the transcriptional control of the vector and can be replicated in a suitable host cell.

Insofar as the present invention describes vectors for manipulating multiple nucleic acid segments in concatamerized units, it is to be understood that the concatamer of vector-insert-vector-insert (etc) can be accomplished by a variety of structures, namely the use of any one of the previously mentioned bacteriophage packaging sites in place of a cos site.

The preparation of such a concatamer in a method of the present invention utilizes a DNA molecule or segment as described earlier for the cos site-containing molecules, but substituting the cos site with one of the other packaging sites. The principle effect of such a substitution is to change the bacteriophage particle into which the concatamer can be packaged, and the packaging extract required to make the packaged concatamer product.

Thus the invention also contemplates a DNA molecule comprising a sequence of nucleotides that defines a bacteriophage packaging site located between ligating means. The ligating means can be any of a variety of means for ligating the packaging site-containing segment into concatamers by combination with a nucleic acid segment as described herein.

Exemplary means include restriction endonuclease sites as discussed earlier that form cohesive termini upon cleavage, oligonucleotide primer binding sites for producing polymerase chain reaction (PCR) products able to incorporate cohesive termini, and the like. The mechanism for producing ligation sites should not be construed to limit the invention insofar as the concept advanced by the present examples is to produce packaged nucleic acid molecules formed by (1) ligation to yield the subject concatamer and (2) subsequent packaging based on the packaging site of the concatamer.

As for the cos site-based DNA molecules, the preferred ligating means in a DNA molecule of this embodiment is provided by restriction endonucleases, particularly those that produce cohesive termini, and more particularly those that direct alternating DNA segment structures.

A DNA segment of the present invention that is less than about 200 nucleotides in length can easily be synthesized by chemical techniques, for example, via the phosphotriester method of Matteucci et al., *J. Am. Chem. Soc.,* 103:3185 (1981) or using phosphoramidite chemistry according to Beaucage et al., *M.H. Tetrahedron Letters,* 22:1859–1862 (1982). Of course, by chemically synthesizing the coding sequence, any desired modifications can be made simply by substituting the appropriate bases for those in the native nucleotide base sequence.

A DNA segment of this invention can also be prepared from a DNA molecule of this invention by subjecting the DNA molecule to restriction endonuclease digestion using the appropriate restriction endonuclease corresponding to the NPRE sites contained on the DNA molecule. Thereafter, the cos-site containing DNA segment is separated from the other DNA fragments produced by the digestion reaction. Typically, the other fragments are of very low molecular weight, typically less than 50 and preferably less than 20 nucleotides in length, and can be separated by ethanol precipitation of the nucleic acids after digestion and recovery of the precipitate. Alternatively, the digest can be resolved by agarose gel electrophoresis to separate the DNA fragments, and the DNA segment can be recovered from the agarose gel as is well known.

Larger DNA segments and DNA molecules of this invention corresponding to, for example, a complete polycos vector, can easily be prepared by ligating smaller oligonucleotides. Typically, single stranded oligonucleotides of between 40–75 nucleotide bases in length are prepared with overlapping complementary ends to form the complete cassette DNA segment. The oligonucleotides are then annealed and the oligos are ligated to form a complete double stranded (ds DNA) molecule or segment. See for example, Urdez et al., *Proc. Natl. Acad. Sci. USA,* 80:7461–7465 (1983); and Hallewell et al., *J. Biol. Chem.,* 264:5260–5268 (1989).

Also contemplated as within the present invention are ribonucleic acid (RNA) equivalents of the above described DNA molecules or segments.

C. Methods to Produce a Library

A library of this invention is a library of bacteriophage particles, each particle containing a DNA molecule comprising a concatamer of alternating sequences that define bacteriophage packaging sites and cloned insert DNA.

An exemplary library utilizes the bacteriophage lambda cos packaging site, and is referred to as a polycos library. The polycos library is produced by using well known in vitro lambda phage packaging reaction conditions to package the unique polycos concatamer described herein.

The preparation of a concatamer suitable for in vitro packaging can be accomplished by a method comprising the following steps.

(1) A first DNA segment of this invention comprising a sequence of nucleotides that defines a bacteriophage packaging site located between first and second termini having ligation means is admixed with a population of preselected second DNA segments in a molar ratio of from about 0.01:1 to about 100:1, respectively, to form a ligation admixture. The second DNA segments are a preselected population of DNA segments to be cloned into the phage library and are from about 10 to about 20,000 nucleotides in length, and preferably are less than 10,000 nucleotides in length. The second DNA segments have first and second termini with ligation means compatible with ligation to the first DNA segments.

In preferred embodiments, the ligation means are cohesive termini, such as are produced by restriction endonuclease digestion. More preferably, the cohesive termini are complementary in manner to facilitate ligation of the first and second DNA segments. In this embodiment the first terminus of the first DNA segment is complementary to the second terminus of the second DNA segment, and the second terminus of the first DNA segment is complementary to said first terminus of said second DNA segment.

To prevent self-ligation, it is preferred that the termini of the first DNA segment are non-complementary. To prevent concatamerization of the first DNA segment to itself it is preferred that the termini of the first DNA segment are non-palindromic.

One embodiment combines all of the above ligation means features to insure directional ligation in a manner that the first and second DNA segments alternate.

To achieve highest ligation efficiencies it is preferred that the molar ratio of the first and second DNA segments be from about 0.1:1 to about 10:1, and most preferably about 1:1.

(2) The ligation mixture is maintained under ligation conditions for a time period sufficient to form a population of DNA molecules each having a nucleotide sequence that comprises (i) at least three and no more than about 100 copies of the first DNA segment, and (ii) at least two of the second DNA segment. Each formed DNA molecule contains alternating first and second DNA segments, i.e., is a concatamer, such that each of the second DNA segments is located between a pair of the first DNA segments.

The ligation conditions are preferably selected to favor hybridization of complementary rather than non-complementary sequences of nucleic acid, such as those found in the cohesive termini of a duplex DNA molecule after digestion by a restriction endonuclease, i.e., under high stringency hybridization conditions. Thus the resulting hybridized first and second DNA segments can be operatively linked according to the orientation defined by the complementarity of their respective cohesive termini, when that complementarity is included in the design of the method.

Preferably, the choice of cohesive termini on the first and second DNA segments is selected as to force the ligation to be directional, namely the alternating first-then-second-then-first DNA segment order is dictated by the complementarity of the cohesive termini. In addition, due to the stringency of hybridization, no stray hybridizations occur to any significant degree. Thus in this embodiment, the resulting concatameric DNA molecule contains substantially all of the first and second DNA segments oriented in a uniform head-to-tail coding direction.

By "substantially all" is meant that greater than 90 percent, and preferably greater than 99 percent, of all ligated DNA segments are present in the cohesive termini directed orientation.

Ligation conditions are conditions well known in the art that promote hybridization and subsequent covalent intermolecular phosphodiester bond formation between adjacent 5' phosphoryl and 3' hydroxyl residues. Ligation conditions include a temperature favorable to a ligation reaction and an aqueous environment containing buffer compatible with enzyme activity, an amount of ligase enzyme sufficient to catalyze the ligation reaction and DNA concentrations of the first and second DNA segments to be joined sufficient to energetically favor hybridization of the cohesive termini. A preferred ligation buffer is 50 mM Tris-Hcl, 7 mM MgCl$_2$, mM DTT, 1 mM ATP. A preferred ligase is T4 DNA ligase. A preferred amount of T4 DNA ligase is in the range of 10 to 0.01 units of T4 DNA ligase per 20 microliter (ul) ligation reaction admixture volume, preferably about 1 to 3 units of T4 DNA ligase. Preferred DNA concentrations are in the range of 5 nanograms (ng) to 5 ug DNA per ul, preferably about 0.2 to 1.0 ug/ul. Higher DNA concentrations are preferred in a ligation reaction to favor concatamer formation. Actual DNA concentrations can vary to produce optimum conditions for concatamer formation depending on the lengths of the DNA molecules to be ligated, as is well known. Preferred temperature of a ligation reaction are in the range of 0° to 37° C., preferably 4° to 30° C. and more preferably about 12° to 22° C.

The ligation admixture is maintained under ligation conditions for a time period sufficient for concatameric polycos DNA to form. The time period required depends, as is well known, on time, temperature, substrate concentrations and enzyme activity. Typical time periods using the preferred ligation conditions are from about 3 minutes to about 48 hours, preferably about 2 to 24 hours and preferably about 16 hours, particularly when ligating at 12° 1 C.

In one embodiment of the methods of this invention, the bacteriophage packaging site is the cos site described earlier. Preferred polycos libraries are prepared as described in the Examples.

The preselected population of DNA segments (second DNA segments) for use in the present methods can be any of a variety of populations of DNA segments, and depend largely on the overall cloning objectives. The second DNA segments can be present as a repertoire of cDNA molecules produced from mRNA, can be produced from genomic DNA by shearing or specific restriction enzyme cleavage to produce DNA segments of the prescribed size. Alternately, the second DNA segments can be formed from a population of random oligonucleotides designed to encode a library of random gene fragments or a library of peptide epitopes for use in epitope mapping studies.

Methods for producing a population of DNA segments for cDNA or genomic cloning are well known and have also been described in *Molecular Cloning: A Laboratory Manual: Second Edition*, Sambrook, et al., Cold Spring Harbor Laboratory Press, Cold Spring Harbor, N.Y. (1989); and in *Current Protocols in Molecular Biology*, Ausubel et al., eds., John Wiley and Sons, N.Y. (1987).

Methods for producing a population of synthetic DNA segments using synthetic oligonucleotides are described at least by Devlin et al., *Science*, 249:404–406 (1990), at note 7; Scott et al., *Science*, 249:386–390 (1990); and Cwirla et al., *Proc. Natl, Acad. Sci. USA*, 87:6378–6382 (1990).

Size selection to yield a population of DNA segments of the required lengths can be accomplished by a variety of sizing means including gel electrophoresis, chromatography differential centrifugation and the like separation techniques.

The production of concatamer-based libraries of bacteriophage as described herein provides a variety of uses. For example, the efficiency of cloning smaller nucleic acid fragments is greatly increased because one can produce multiple clones in a single bacteriophage particle. Where the objective is to transfer nucleic acid fragments into a host cell, such as in a transfection or transformation of eukaryotic or prokaryotic cells, a single bacteriophage particle delivers multiple fragments.

Thus the use of a polycos library provides a means to deliver higher copy numbers of fragments into a host cell, where the copy number depends on the number of unit copies in a single concatameric DNA molecule packaged in each bacteriophage particle. The number of units per particle depends, as described herein, on the bacteriophage particle's capacity and the size of the second DNA segment being concatamerized by the first DNA segment carrying the packaging site.

A related embodiment of the present invention contemplates a method for producing a polycos library in the form of a population of lambda phage particles containing the above described polycos concatamers. The method comprises the steps of:

(1) preparing a population of DNA molecules comprising the polycos concatamer described above;

(2) forming a lambda packaging reaction admixture by combining the population of DNA molecules with an in vitro lambda packaging extract in an amount sufficient to package a plurality of DNA molecules; and (3) maintaining the lambda packaging reaction admixture under lambda packaging conditions for a time period sufficient to package a plurality of the DNA molecules and form a plurality of lambda phage particles that each contain at least one DNA molecule, thereby forming said polycos library.

In vitro lambda packaging extracts are widely used and extensively well characterized. See, Enquist et al., *Meth. Enzymol.*, 68:281–298 (1979); *Molecular Cloning: A Laboratory Approach, Second Edition*, Sambrook et al., eds., Cold Spring Harbor Laboratory Press, Cold Spring Harbor, N.Y. (1989); and *Current Protocol in Molecular Biology*, Ausubel et al., eds., John Wiley and Sons, N.Y. (1987) for descriptions of the preparation and use of lambda packaging extracts. Extracts are also available from a variety of commercial vendors including Stratagene (La Jolla, Calif.) and Promega (Madison, Wis.).

Ratios of packaging extract to input DNA molecules containing polycos for packaging can vary widely, and depend on the quality of the packaging extract and the size of the library to be produced. Because a basic objective of polycos vectors is to increase the lambda phage library produced, it is preferred that the packaging extract have a capacity to form at least $1 \times 10^8$ plaques per ug of wild type lambda DNA, preferably at least $1 \times 10^9$ plaques per ug, and more preferably at least about $2 \times 10^9$ plaques per ug.

A lambda packaging reaction admixture contains an amount of packaging extract sufficient to package the input polycos DNA. A typical and preferred amount of extract is an amount present in twenty five microliters (ul) that packages at least $1 \times 10^8$ plaques per ug of wild-type lambda DNA when the DNA is present in 4 ul. Thus, for extracts having a capacity of $1 \times 10^8$ plaques per ug of wild-type lambda DNA per 25 ul of extract, an amount of 6 ug of polycos concatameric DNA molecules down to about 10 nanograms (ng) of concatameric DNA can be packaged, preferably about 1 ug of concatameric DNA.

Lambda packaging conditions combine variables of temperature, buffer, substrate and pH formulated to produce assembly and packaging of bacteriophage lambda particles, are all well known, and are not to be taken as limiting in practicing the present methods. See for example, the packaging conditions described in *Molecular Cloning: A Laboratory Manual*, Maniatis et al. eds., Cold Spring Harbor Laboratory Press, Cold Spring Harbor, N.Y. (1982). Typical conditions comprise combining recently thawed extracts in a volume of 25 ul with about 1 ug concatamerized DNA in 5 ul of TM buffer (10 mM Tris-HCl, pH 8.0, 10 mM $MgCl_2$) to form a DNA-extract admixture. The admixture is then maintained at room temperature for 1 hour to allow the DNA to be packaged into the bacteriophage particles. The packaged particles are then diluted in SM buffer and plated onto host cells as described in Example 2b. Optimum conditions recommended by the manufacturer of the packing extract are particularly preferred to insure the maximum packaging efficiencies.

The lambda phage library (polycos library) prepared by the above methods can be used according to conventional methods for propagating a lambda phage library, for screening the library, for plaque purifying individual phage particles containing one or more DNA inserts of interest, and for preparation of stocks of isolated phage particles for producing isolated nucleic acid from the stock for subsequent manipulation and cloning. These general recombinant DNA manipulations are not part of the present invention, are well known in the art and are recited to merely identify the scope and context of the present invention. Exemplary manipulations, including packaging of lambda particles and titration of infectious units of phage in the library to measure the library size, and Ff helper rescue to produce a library of Ff particles each containing individual DNA inserts are described in the Examples.

D. Kits for Preparing a Polycos Library

Many of the reagents described herein (e.g., nucleic acids such as primers, vectors, and the like) have a number of forms, and in equilibrium with each other. As the skilled practitioner will understand, representation herein of one form of a compound or reagent is intended to include all forms thereof that are in equilibrium with each other.

The reagents described herein can be packaged in kit form. As used herein, the term "package" refers to a solid matrix or material customarily utilized in a system and capable of holding within fixed limits one or more of the reagent components for use in a method of the present invention. Such materials include glass and plastic (e.g., polyethylene, polypropylene and polycarbonate) bottles, vials, paper, plastic and plastic-foil laminated envelopes and the like. Thus, for example, a package can be a glass vial used to contain the appropriate quantities of a DNA molecule of the present invention for preparing a polycos library or phage library of the present invention. An appropriate quantity of DNA molecules in a kit of this invention is an amount sufficient to prepare at least one phage library according to the present methods.

Kits useful for producing a phage library of DNA molecules according to the present invention also typically include, in separate containers within the kit, ligase, ligation buffer (in concentrated or 1× strength), helper phage, and other like agents for performing the methods of the present invention.

Kits can also comprise a preassembled library based on concatamerized DNA molecules, or bacteriophage particles containing concatamers.

The reagent species of any system described herein can be provided in solution, as a liquid dispersion or as a substantially dry powder, e.g., the plasmids may be provided in lyophilized form.

EXAMPLES

The following description provides details of the manner in which particular embodiments of the present invention may be made and used. This description, while exemplary of the present invention, is not to be construed as specifically limiting the invention. Variations and equivalents, now known or later developed, which would be within the understanding and technical competence of one skilled in this art are to be considered as falling within the scope of this invention.

1. Preparation of a DNA Molecule Having a Cos Site

To demonstrate the polycos vector system, a lambda cos site-containing DNA segment was cloned into the multiple cloning site of a derivative (phagescript SK) of the filamentous phage M13mp19 described by Yanisch-Perron et al., *Gene*, 33:103 (1985). Phagescript SK (Stratagene, La Jolla, Calif.), was digested with the restriction endonucleases BamHI and XbaI to release the small 12 nucleotide base pair (bp) fragment from the polylinker region and form a linear phagescript molecule. The linearized molecule was then ethanol precipitated to separate the small fragment, and the 7.3 kilobase (kb) linear phagescript molecule in the precipitate was recovered. Restriction enzyme digestions, ethanol precipitation and other routine and well know DNA manipulations were conducted according to the methods described in *Molecular Cloning: A Laboratory Manual, Second Edition*, Sambrook et al., eds., Cold Spring Harbor Laboratory Press, Cold Spring Harbor, N.Y. (1989).

A plasmid designated pOU61Cos that contained the cos site on a BamHI-XbaI-fragment of the plasmid was obtained from Dr. Brownlee (Oxford University, Oxford, UK) and was digested with the restriction endonucleases BamHI and XbaI to release the cos site-containing fragment. The fragment was recovered and ligated to the linear phagescript molecule described above to form a circular plasmid designated phagescript-cos. Phagescript-cos contains a single cos site together with genes I through X derived from wild type M13 filamentous phage, a polylinker region adjacent to a Lac Z gene from cloning DNA segments into a Lac Z-fusion protein-encoding gene, the M13 origin of replication and M13 packaging site, and both T3 and T7 bacteriophage promoters for initiating DNA transcription.

2. Polycos Vector Cloning of Multiple DNA Segments Into A Single Bacteriophage Particle a. Preparation of a Polycos Concatamer Phagescript-cos DNA prepared in Example 1 was isolated by standard double-stranded M13 miniprep procedures and was digested with the restriction endonuclease BamHI to form a linear phagescript-cos DNA molecule. The linear molecule was ethanol precipitated and the precipitate was resuspended at about 20 nanogram (ng) per microliter (ul) of TE (10 mM Tris-HCl, mM EDTA, ph 8.0). Control phagescript was also linearized and resuspended in TE. Both linear molecules were separately ligated into self-concatamers by incubating the molecules at 5 degrees C. (5C.) for 16 hours in a ligation reaction admixture containing linear molecule at 0.125 ug/ul in 1× ligation buffer (50 mM Tris-HCl, pH 7.5, 7 mM $MgCl_2$, 10 mM beta-mercaptoethanol), 1 mM ATP and 0.4 units T4 DNA ligase. The resulting phagescript-cos concatamer represents a large DNA molecule comprising multiple cos sites having approximately 7.3 kb of DNA inserted between each cos site of the concatamer. The control concatamer contains no cos sites.

b. Packaging Polycos-Containing Concatamers Into Bacteriophage Lambda

Ligation reaction admixture containing concatameric phagescript-cos, or control concatamers, prepared in Example 2b were packaged into bacteriophage lambda particles using well known procedures. See, for example the in vitro packaging methods described in *Molecular Cloning: A Laboratory Manual: Second Edition*, Sambrook et al., Cold Spring Harbor Laboratory Press, Cold Spring Harbor, N.Y. (1989). Specifically, the ligation reaction admixture product containing approximately 0.5 ug concatameric phagescript-cos in 4 ul of ligation reaction admixture was combined with 25 ul of commercially available Gigapack II Gold lambda packaging extract from Stratagene to form a packaging reaction admixture and packaged according to the manufacturer's specifications for 1.75 hours to form a library of phage particles. Thereafter, 500 ul of SM broth (5.8 grams(gm) NaCl, 2 gm $MgSO_4 7H_2O$, 50 mM Tris-HCl, 0.01% gelatin, pH 7.5) was added to the packaging reaction admixture, and 20 ul of chloroform was added to inactivate any M13 particles and to kill any *E. coli* cells present. Either 450 ul, 10 ul or 1 ul of the resulting SM broth/packaging reaction admixture was combined with 200 ul of a exponentially growing *E. coli* XL1-Blue host cells (Stratagene) and maintained at 37° C. for 10 minutes to allow the phage to absorb to the bacterial cells. The resulting phage-*E. coli* admixture was admixed with 2 mls of molten (45C.) top agar (5 gm/liter(L) NaCl, 2 gm/L $MgS_4$, 5 gm/L yeast extract, 10 gm/L NZ amine and 7 gm/L agar), and poured for even distribution of the top agar onto prewarmed (37C.) bacterial agar plates (5 g/L NaCl, 2 gm/L $MgSO_4$, 5 g/L yeast extract, 10 gm NZ amine (casein hydrolysate) and 25 g/L Difco agar). The plates were maintained at 37C. for 12 to 24 hours during which time lambda phage particles grew into plaques on the bacterial lawn. Using phagescript-cos derived phage particles, a plaque is defined as a region of slowed *E. coli* growth due to the presence of the phagescript-cos genome in the bacterial cell. The number of phages were counted to determine the total number of plaque forming units (pfu) present per ml of original concatamer-containing phage library. The results are shown in Table 2 below.

TABLE 2

Packaging of Polycos-containing Concatameric DNA Molecules

| DNA Sample[a] | DNA (ug) | Plaques (#) | pfu/ml |
|---|---|---|---|
| Phagescript | .18 | 0 | 0 |
|  | .004 | 0 | 0 |
|  | .0004 | 0 | 0 |
| Phagescript-cos(1) | .11 | 560 | 1244 |
|  | .0025 | 10 | 1000 |
|  | .00025 | 0 | 0 |
| Phagescript-cos(2) | .11 | 200 | 444 |
|  | .0025 | 2 | 200 |
|  | .00025 | 0 | 0 |

[a]Two separate phagescript-cos plasmids (1) and (2) from different mini preps were tested in the packaging reaction.

As shown in Table 2, the control plates prepared using phagescript without any cos sites did not contain plaques, whereas the plates prepared using phagescript-cos contained large numbers of plaques. The presence of plaques indicates that the phagescript-cos DNA concatamers containing multiple cos sites were properly packaged into infectious phage particles. The two to three fold difference in efficiency between the two polycos samples reflects the difference in the quality or quantity of DNA used to prepare concatamers. The variability arose since double stranded M13 miniprep DNA was used in this procedure to produce phagescript-cos for preparing concatamers. In similar tests, the yield of polycos-packaged inserts obtained was about $3 \times 10^8$ copies of individual inserts per ug of concatamer.

By calculating the vector and insert size using the model polycos system described here, and using estimates that (1) phagescript-cos linear DNA is about 7.3 kb, and (2) lambda packages about 38 to 51 kb, or an average size of about 45 kb, the above data in Table I indicates that the above polycos vectors system packaged about 6 inserts per phage particle. Although phagescript was used in the present assay, other, polycos vectors can be prepared that are in the size range of about 1 to 26 kb. Thus, depending on the polycos vector utilized, and the size of the inserted DNA segment into the concatamer, phage particles can be prepared that contain up to as many as 2 to 50 different DNA segments.

The simplicity of the polycos vectors system for producing libraries is that lambda packaging and infection of E. coli cells to form a library is accomplished with the concatameric "polycos" DNA to yield phage particles having multiple inserts of cloned DNA segments.

3. Preparation Of A Polycos Vector Having Two Non-Palindromic Restriction Endonuclease Sites That Are Non-complementary The efficiency of cloning a library, when expressed as a number of library members per input DNA segment, depends on the quality of the concatameric polycos DNA produced for packaging into lambda particles. To eliminate insert-to-insert or vector-to-vector ligation in the formation of polycos-containing concatamers, the polycos vector is preferably designed to contain two non-palindromic restriction endonuclease sites that are not complementary to each other. This design forces directional "head-to-tail" orientation and prevents ligation of vector to itself. By preparing insert DNA with the appropriate cohesive termini complementary to the polycos vector ends, insert also cannot ligate to itself. By this design, maximum numbers of insert DNA are packaged per input cos sites in the concatamer, thereby maximizing the possible number of inserts packaged.

As an example, a polycos vector containing two BstXI restriction endonuclease sites is prepared such that the two BstXI sites are (1) both non-palindromic and (2) when cleaved by BstXI do not form complementary cohesive termini on the linear polycos DNA vector (i.e., are non-palindromic). To that end, lambda bacteriophage DNA (ATCC #23724-B2) is digested with Hind II to produce a mixture of lambda DNA segments. M13mp19 described by Yanish-Perron et al., Gene, 33:103–119 (1985) and available at least from United States Biochemical Corporation, Cleveland, Ohio) is digested with Hind II to form linearized M13 mp19. Thereafter, linearized M13 mp19 is admixed with the mixture of lambda DNA segments to form a ligation admixture having 0.2 ug M13mp19DNA, 1 ug lambda DNA, 1 unit T4 DNA ligase and 1x ligation buffer in a volume of 20 ul, and maintained at 4C. for 1 hour to allow formation of a ligation product.

Four ul of ligation product is admixed with 25 ul of Gigapack Gold II lambda packaging extract (Stratagene) and the resulting admixture is packaged according to the manufacturers directions, and plated with XL1-Blue host cells as described before. Only constructs (vectors) containing the lambda Hind II DNA segment that encodes the cos site will be packaged according to the methods of this invention. Phage containing these constructs are designate M13-cos phage particles and the vector is designated M13-cos. The vector M13-cos is then modified by site-directed mutagenesis to introduce the two BstXI sites into the M13-cos vector to form M13-cos/BstXI.

Site-directed mutagenesis is performed using a site-directed mutagenesis kit (Biorad Laboratories, Richmond, Calif.) and Biorad's instructions provided with that kit together with the procedures and some materials provided in the pBluescript/II phagemid kit (Stratagene). Briefly, the single-stranded template required for the site-directed mutagenesis procedure is prepared first by maintaining a 5 ml culture of XL1-Blue cells (Stratagene) containing the M13-cos vector at 37C. for 3 hours. One ul of a solution containing $1 \times 10^{11}$ plaque forming units (pfu) per ml of VCS-M13 helper phage (Stratagene) are then added to the 5 ml culture and the culture is further maintained at 37C. for 3 hours. Helper phages, R408 or M13K07, can also be used in this invention and are commercially available from Promega Corp. (Catalog Number P2450, Madison, Wis.). During this time, single-stranded M13 phage containing the single-stranded M13-cos DNA are formed and released from the XL1-Blue bacteria.

The bacteria in this culture are killed by heating the culture to 68° C. (68C.) for 15 minutes. The killed bacteria are removed from culture, by centrifuging the culture at 10,000 x g to produce a supernatant containing the single-stranded phage. One ml of this supernatant is added to a previously established 5 ml culture of CJ236 bacteria (Biorad Laboratories, Richmond, Calif.) that is in the late log phase of growth. The culture is maintained at 37C. for 10 minutes and then 10 ul of the culture is plated onto LB bacterial plates (LB media contains 10 g/L of bactotryptone, 5 g/L of yeast extract, 5 g/L of NaCl containing both 50 ug/ml of ampicillin and 30 ug/ml of chloramphenicol. The resulting bacterial plates are maintained at 37° C. for 12–18 hours allowing formation of individual colonies of CJ236 bacteria containing the single-stranded M13-cos phage.

One of the resulting colonies is selected and used to initiate a 5 ml bacterial culture in superbroth media consisting of 35 g/L bactotryptone, 20 g/L yeast extract, 5 g/L sodium chloride at pH 7.5. This 5 ml culture is maintained at 37C. for 6 hours and then transferred to 150 mls of superbroth in a 250 ml flask and further maintained at 37C.

for one hour with constant shaking. Then 100 ul of a solution containing 1×10¹¹ PFU/ml of VCS-M13 helper phage (Stratagene) is added to the culture and the culture was maintained at 37C. for 12–18hours with constant shaking. During this time, a culture of CJ236 bacteria containing the single-stranded DNA template is produced.

This culture is then used to isolate the M13-cos single-stranded template using the single-stranded phage DNA isolation procedures described in the p Bluescript/ II manual (Stratagene). Briefly, 1.5 ml of the culture containing M13-cos single-stranded phage produced above is centrifuged at 17,000 xg to produce a clarified supernatant. Approximately 1.2 ml of this supernatant is transferred to an eppendorf centrifuge tube and 300 ul of a solution containing 3.5M Ammonium Acetate at PH 7.5 and 20% polyethylene glycol (PEG) is admixed to it. The resulting admixture is maintained at 25C. for 15 minutes. The admixture is centrifuged at 11,000 x g for 20 minutes to pellet the single-stranded phage present. The resulting supernatant is removed from the phage pellet.

The phage pellet is resuspended in 300 μl of TE buffer consisting of 10 mm Tris-HCl at pH 8.0 and 1 mm EDTA. The resulting solution is admixed with an equal volume of phenol/chloroform and the resulting aqueous phase transferred to a fresh tube. The aqueous phase is reextracted with phenol/chloroform until no significant interface between the organic and aqueous phase is observed. The aqueous phase is then admixed with an equal volume of chloroform and the single-stranded DNA is isolated from the aqueous phase by ethanol precipitation using Ammonium Acetate.

The amount of single-stranded M13-cos isolated is determined by gel electrophoresis. This single-stranded M13-cos DNA was then used as a template in the site-directed mutagenesis procedure below.

mutagenesis reaction is terminated by adding 1 ul of a solution containing 50 mM ethylene diaminetetraacetic acid (EDTA) to form the DNA molecule M13-cos/BstXI.

The mutagenesis reaction admixture (10 ul) is then transformed into competent XL1-Blue host cells using the instructions provided by the manufacturer of these competent cells (Stratagene). The circular plasmid DNA form of M13-cos BstXI is isolated from the resulting transformants using the DNA isolation procedures of Sambrook et al., *Molecular Cloning: A Laboratory Manual, Second Edition,* Cold Spring Harbor Laboratory, Cold Spring Harbor, New York, New York (1989). The accuracy of the above site-directed mutagenesis procedure in forming M13-cos/BstXI was confirmed by restriction endonuclease digestion with BstXI.

4. Preparation of Other Polycos Vectors

To demonstrate other permutations of a polycos-based library, polycos vectors were developed with different combinations of cohesive termini.

To that end, Phagescript SK from Example 1 was subjected to crossover PCR as before using primers to introduce a BssHI site between the M13 ori and the pII gene, and to introduce an amber codon in the pII gene to form plasmid M13704.

Plasmid M13704 was subsequently subjected to crossover PCR to insert the cos fragment from Example 1 at the BssHI site to form plasmid MPAK.

Plasmid MPAK was modified to insert a polylinker into the SmaI site between the ampicillin resistance gene and the cos site to form M13SBB having a single EcoRI site, which can be linearized using EcoRI to form a cos-based DNA segment of this invention with cohesive EcoRI termini.

TABLE 3

| Oligonucleotide Sequence |
|---|

Oligonucleotide p1
5-TAT GGG GTT TTG CCA GAC AAC TGG AAC
    AGT TTC AGC GGA GTG CCA GTA GAA
    TGG AAC AAC TAA AGG-3'
              (SEQ ID NO 3)

The site-directed mutagenesis reaction used to produce two BstXI sites in M13-cos is carried out in the following manner. Briefly, 5 ug of the M13-cos single-stranded template DNA prepared above is admixed with 50 ng of kinased oligonucleotide p1, having the nucleotide base sequence shown in Table 3; SEQ. ID. NO. 3, that is synthesized on an Applied Biosystem oligonucleotide synthesizer, Model 381A, (Applied Biosystems, Foster City, Calif.), and is kinased on the synthesizer according to the manufacturer's instructions, as a kinased oligonucleotide to form a 10 ul admixture. This admixture is maintained at 68C. for 10 minutes and then 25C. for 5 minutes to allow the oligonucleotide to anneal to the single-stranded template. The DNA strand containing the oligonucleotide p1 (Table 3) is synthesized by adding 4 ul of a solution containing 10 mM of adenosine triphosphate (rATP), 4 ul of a buffer containing 0.66 M Tris-HCl at pH 7.6, 50 mM MgCl₂, 50 mM dithiothreitol (DTT), 2 ul of a solution containing 2.5 mM each of dCTP, dATP, dGTP and dTTP, 1 ul of T4 DN4 ligase (Stratagene), 1 ul of DNA polymerase 1 Klenow fragment (Stratagene) to form a mutagenesis reaction admixture. This admixture is maintained at 37° C. for ninety seconds. The Plasmid MPAK was modified to insert a second Bgl II site and form TTV3BstXI. Cleavage of TTV3BstXI with Bgl II removes a neutral stuffer fragment of about 1 kb, and forms a linear cos-based DNA segment with cohesive Bgl II termini. Cleavage of TTV3BstXI with BstXI removes a small stuffer fragment, and the remaining termini on the linear cos vector are non-palindromic, non-complementary BstXI termini.

Plasmid MPAK was also modified to insert a polylinker having both a single EcoRI site and a single KpnI site about 100 nucleotides apart, forming plasmid 970-3. Double digestion of 970-3 with EcoRI and KpnI removes a single small approximately 100 bp stuffer fragment to form a linear cos-based DNA segment with a first cohesive EcoRI terminus (5' overhang) and a second cohesive KpnI terminus (3' overhang).

Concatamer ligation reactions were conducted, followed by lambda packaging reaction as described earlier, using the above linearized cos-based vectors and certain inserts as described below.

When a double-stranded synthetic oligonucleotide having EcoRI termini was concatamerized with the linearized M13SBB, the packaging efficiency of the concatamer produced was $1.5 \times 10^8$ plaque forming units (pfu) per microgram (ug) of input concatamer. Thirty-three percent of the colonies had insert. These data indicate that a cos-based vector using complementary cohesive termini of a two base overhang on both the first (vector) and second (insert) DNA segments provided high packaging efficiency.

When a single-stranded synthetic oligonucleotide having a first terminus complementary to an EcoRI overhang, and a second terminus complementary to a KpnI overhang was concatamerized with the linearized 970-3, the packaging efficiency of the concatamer produced was $8.3 \times 10^4$ pfu per ug of input concatamer. These data indicate that a cos-based vector using non-complementary termini and having a two base overhang between the double-stranded vector and the single-stranded insert DNA segments provided a measurable packaging efficiency, albeit lower than above.

When the same 970-3 vector was ligated with a double-stranded molecule having EcoRI and KpnI overhangs, the efficiency increased to $2.1 \times 10^6$ pfu per ug of input concatamer.

When the Bgl II-linearized TTV3BstXI vector was ligated with its own Bgl II stuffer fragment, ligation efficiencies of $2.1 \times 10^6$ pfu per ug of input concatamer were observed, and 100 percent of the colonies isolated had insert. Thus equal molar ratios of stuffer and vector yield high efficiency, even where there are complementary palindromic termini on both the first and second DNA segments.

In contrast, when the BstXI-linearized TTV3BstXI was ligated with a double-stranded DNA segment having non-complementary, non-palindromic termini, which are directionally complementary to the vector, an efficiency of $7.4 \times 10^4$ pfu per ug of input concatamer were observed. Thus, directional cloning was demonstrated at useful packaging efficiencies.

A ligation reaction was developed to control the ligation of insert to vector DNA such that unwanted vector-vector ligations could be blocked.

To that end, the insert was designed such that the overhangs of the insert are complementary to the vector. The vector itself has non-complementary overhangs and the insert itself has non-complementary overhangs, so that neither can self-circularize. In addition, the overhangs are selected such that the combination of the complementary hybridization of a vector overhang with an insert overhang does not form the restriction site used to produce the respective termini. Thus, their proper ligation "kills" the original site, and forms a new site. In contrast, the end-to-end ligation of a vector recreates the original site, for example a KpnI site. In that ligation reaction, in addition to the normal ligation reactants, restriction enzyme KpnI was included to cut unwanted end-to-end ligation of the vector, but not disturb the ligation product between vector and insert that "kills" a KpnI site.

Using the restriction enzyme-containing ligation reaction, the vector 970-3 linearized with EcoRI and KpnI, and an insert with "killer" EcoRI and KpnI termini, a ligation efficiency of $4.8 \times 10^5$ pfu was observed in the absence of the enzyme KpnI, and $5 \times 10^6$ pfu efficiency was observed in the presence of KpnI. Thus a 10-fold increase of ligation efficiency was observed when a killer enzyme strategy was utilized to block unwanted ligation reactions.

These results demonstrate that a variety of formats for producing a concatameric library using polycos are available using the methods of the present invention.

The foregoing is intended as illustrative of the present invention but not limiting. Numerous variations and modifications can be effected without departing from the true spirit and scope of the invention.

What is claimed is:

1. A method of producing a phage library of DNA molecules comprising the steps of:
   (a) admixing in a ligation buffer a first DNA segment comprising a sequence of nucleotides that defines a bacteriophage packaging site located between first and second termini capable of being ligated, with a population of preselected second DNA segments in a molar ratio of from about 0.01:1 to about 100:1, respectively, to form a ligation admixture, said second DNA segments being from about 10 to about 20,000 nucleotides in length, said second DNA segments having first and second termini ligatable with said first DNA segment;
   (b) maintaining said ligation admixture under ligation conditions for a time period sufficient to ligate said termini and form a population of concatamerized DNA molecules each having a nucleotide sequence that comprises (i) at least three and no more than 50 copies of said first DNA segment, and (ii) at least two of said second DNA segments;
   (c) forming a bacteriophage packaging reaction admixture by combining the population of concatamerized DNA molecules with a bacteriophage packaging extract in an amount sufficient to package a plurality of the concatamerized DNA molecules; and
   (d) maintaining the bacteriophage packaging reaction admixture under packaging conditions for a time period sufficient to package a plurality of the concatamerized DNA molecules and form a plurality of bacteriophage particles each containing at least one DNA molecule, thereby forming said phage library.

2. The method of claim 1 wherein said bacteriophage packaging site is a bacteriophage lambda cos site.

3. The method of claim 1 wherein said termini are cohesive, complementary termini.

4. The method of claim 1 wherein said first terminus of said first DNA segment is complementary to said second terminus of said second DNA segment, and said second terminus of said first DNA segment is complementary to said first terminus of said second DNA segment.

5. The method of claim 4 wherein said termini on said first DNA segment are non-complementary cohesive termini.

6. The method of claim 4 wherein said termini on said first DNA segment are non-palindromic cohesive termini.

7. The method of claim 1 wherein each of said second DNA segments are located in said concatamerized DNA molecule between a pair of said first DNA segments such that said first and second DNA segments alternate in said concatamerized DNA molecule.

8. The method of claim 1 wherein said first DNA segment further contains a filamentous phage origin of replication located between said first and second termini.

9. The method of claim 1 wherein said first DNA segment further contains a filamentous phage packaging site located between said first and second termini.

10. The method of claim 1 wherein said first DNA segment further contains a procaryotic origin of replication located between said first and second termini.

11. The method of claim 1 wherein said molar ratio of step (a) is 1:1.

12. A concatameric polynucleotide comprising (i) a plurality of essentially identical first DNA segments, wherein each first DNA segment comprises a bacteriophage packaging site from a bacteriophage, (ii) a plurality of second DNA segments, wherein each of said first DNA segments is flanked by two of said second DNA segments and each of said second DNA segments is flanked by two of said first DNA segments, wherein the total length of a first DNA segment and a second DNA segment is less than the minimum packaging requirement for the bacteriophage.

13. A concatameric DNA according to claim 12, wherein the packaging site is a cos site and the bacteriophage is lambda.

14. A polynucleotide according to claim 12, wherein each first DNA segment comprises a filamentous phage origin of replication.

15. A polynucleotide according to claim 14, wherein the origin of replication is selected from the group consisting of f1, fd, and M13 origins of replication.

16. A polynucleotide according to claim 15, wherein the origin of replication is the f1 origin of replication having a nucleotide sequence shown in SEQ ID NO:2 from base 1 to base 461.

17. A bacteriophage particle comprising a concatameric polynucleotide according to claim 12.

18. A bacterium comprising the concatameric polynucleotide of claim 12.

* * * * *